(12) United States Patent
Ohba et al.

(10) Patent No.: US 6,671,942 B2
(45) Date of Patent: Jan. 6, 2004

(54) METHOD FOR MANUFACTURING A GAS SENSOR

(75) Inventors: Yukio Ohba, Nagoya (JP); Akira Nishimatsu, Mie-ken (JP)

(73) Assignee: Denso Corporation, Kariya (JP)

( * ) Notice: Subject to any disclaimer, the term of this patent is extended or adjusted under 35 U.S.C. 154(b) by 104 days.

(21) Appl. No.: 10/106,241

(22) Filed: Mar. 27, 2002

(65) Prior Publication Data

US 2002/0153250 A1 Oct. 24, 2002

(30) Foreign Application Priority Data

Mar. 28, 2001 (JP) ........................................ 2001-093411

(51) Int. Cl.$^7$ ................................................ B23P 11/00
(52) U.S. Cl. .................. 29/428; 29/DIG. 31; 204/424; 204/431; 73/31.05
(58) Field of Search ............................. 29/888.3, 419.1, 29/428, 506, DIG. 31; 204/424, 425, 429, 431; 73/31.05

(56) References Cited

U.S. PATENT DOCUMENTS 6,319,378 B1 * 11/2001 Kojima et al. .............. 204/427
6,327,891 B1 * 12/2001 Noda et al. ................. 73/31.05
6,408,680 B2 * 6/2002 Friese et al. ................ 73/31.05
6,418,777 B1 * 7/2002 Noda et al. ................. 204/424
6,446,489 B2 * 9/2002 Asai et al. .................. 73/31.05
6,510,728 B2 * 1/2003 Matsuo et al. .............. 204/424
6,546,783 B2 * 4/2003 Shirai ......................... 204/424

FOREIGN PATENT DOCUMENTS

JP          10-10082          1/1998

* cited by examiner

*Primary Examiner*—David P. Bryant
(74) *Attorney, Agent, or Firm*—Nixon & Vanderhye P.C.

(57) ABSTRACT

A hardened powder ring, being a hardened block of talc powder, is inserted into an annular end space between a housing and a sensing element. A pushing member presses and crashes the hardened powder ring into talc powder, thereby stuffing the talc powder into the annular end space. An inner radius $r_p$ and an outer radius $R_p$ of the pushing member have the relationship 0.275 mm $\leq r_p - R_e \leq$ 0.375 mm and 0.15 mm $\leq r_h - R_p \leq$ 0.25 mm with respect to an outer radius $R_e$ of the sensing element and an inner radius $r_h$ of the housing. A press portion of pushing member has an inner curved surface having a curvature radius of 0.3~0.4 mm and an outer curved surface having a curvature radius of 0.3~0.5 mm.

10 Claims, 7 Drawing Sheets

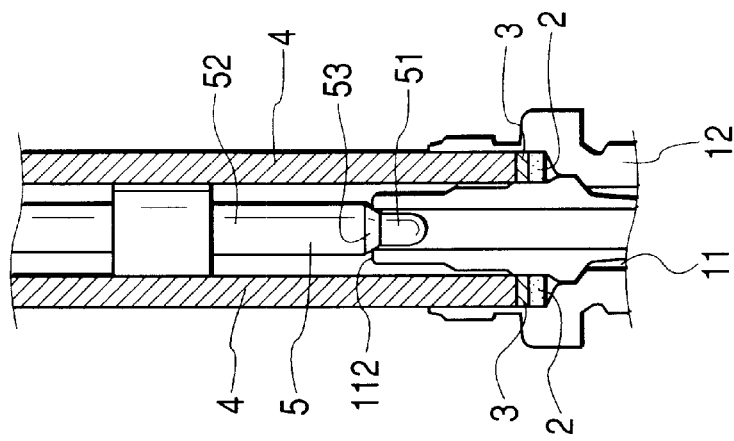
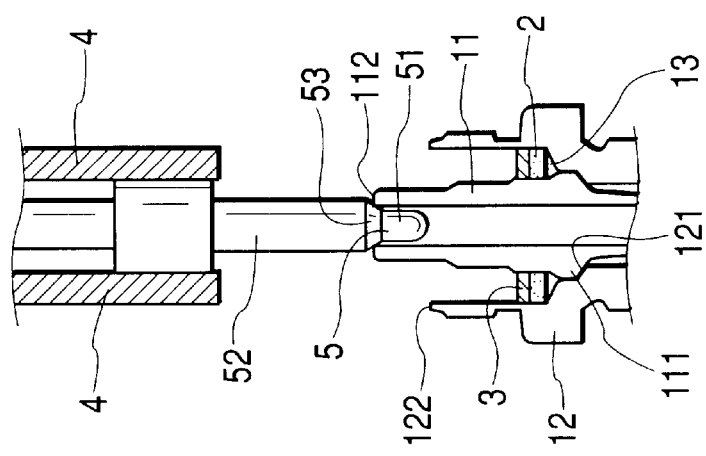
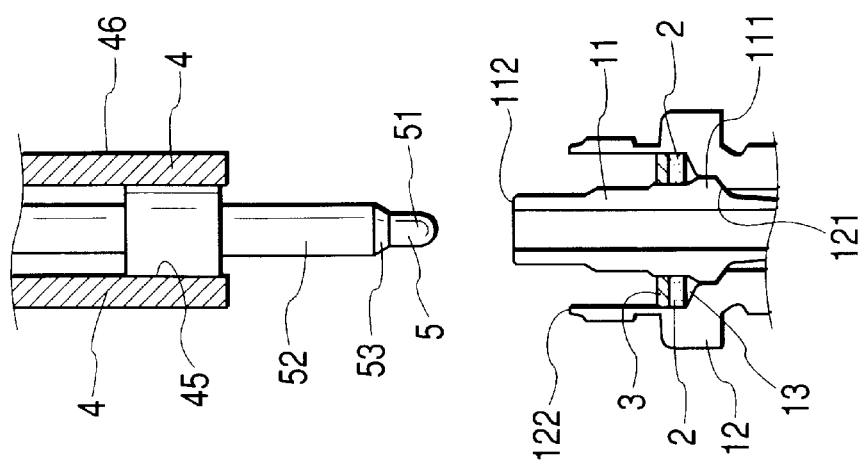

METHOD FOR MANUFACTURING A GAS SENSOR

BACKGROUND OF THE INVENTION

This invention relates to a method for manufacturing a gas sensor having a tubular housing and a sensing element disposed in this housing.

For example, an oxygen sensor or a comparable gas sensor is equipped in an internal combustion engine to measure an oxygen concentration. This sensor comprises a tubular housing and a sensing element disposed in the housing. The housing has an inner cylindrical stepped portion protruding radially inward from an inner cylindrical surface thereof. The sensing element has a flange portion protruding radially outward from an outer surface thereof. The flange portion of the sensing element is placed on the inner cylindrical stepped portion of the housing. Talc powder or other inorganic powder is stuffed into a contact portion between the sensing element and the housing.

In stuffing such inorganic powder into the contact portion, a hardened powder ring is inserted into an annular end space defined between the inner cylindrical surface of the housing and the outer surface of the sensing element. The hardened powder ring is a hardened block of inorganic powder configured into a ring shape. The hardened powder ring is pressed and crushed.

However, according to the above-described conventional gas sensor manufacturing method, it is difficult to uniformly apply a pressing force to the hardened powder ring or the inorganic powder stuffed into the annular end space. This leads to nonuniform density distribution of the inorganic powder in the annular end space. Airtightness will be worsened.

Furthermore, in the pressing operation of the hardened powder ring, the pushing member may accidentally hit or collide with the sensing element or the housing and accordingly may damage the sensing element or the housing. If the sensing element is damaged, the output characteristics of the gas sensor will possibly deteriorate. If the housing is damaged, a small or sliced piece of housing material may mix into the inorganic powder. This will cause insulation defectiveness or other problem.

SUMMARY OF THE INVENTION

In view of the foregoing problems of the prior art, the present invention has an object to provide a manufacturing method for a gas sensor according to which no damage is given to the sensing element or the housing and the inorganic powder can be uniformly stuffed into the annular end space between the sensing element and the housing.

To accomplish the above and other related objects, the present invention provides a first method for manufacturing a gas sensor having a tubular housing and a sensing element disposed in the housing. The first manufacturing method of this invention comprises a step of inserting the sensing element into the tubular housing from a rear end toward a front end of the housing. The sensing element has a flange portion protruding radially outward from an outer surface thereof, and the housing has an inner cylindrical stepped portion protruding radially inward from an inner cylindrical surface thereof. The first manufacturing method of this invention further comprises a step of placing the flange portion of the sensing element on the inner cylindrical stepped portion of the housing, and a step of inserting a hardened powder ring into an annular end space defined between the inner cylindrical surface of the housing and the outer surface of the sensing element. The hardened powder ring is a hardened block of inorganic powder configured into a ring shape. The first manufacturing method of this invention further comprises a step of pressing the hardened powder ring toward the front end of the housing by a tubular pushing member and crushing the hardened powder ring into inorganic powder by the tubular pushing member so that the annular end space is stuffed by the inorganic powder. According to the first manufacturing method of this invention, the following relationship is satisfied $$0.275 \text{ mm} \leq r_p - R_e \leq 0.375 \text{ mm},$$

and $$0.15 \text{ mm} \leq r_h - R_p \leq 0.25 \text{ mm},$$

where $r_p$ represents an inner radius of the pushing member, $R_p$ represents an outer radius of the pushing member, $r_h$ represents an inner radius of the housing, and $R_e$ represents an outer radius of the sensing element at a portion substantially defining the annular end space.

This invention has the following functions and effects.

According to this invention, the inner radius $r_p$ and the outer radius $R_p$ of the pushing member satisfy the relationship $0.275 \text{ mm} \leq r_p - R_e$ and $0.15 \text{ mm} \leq r_h - R_p$ with respect to the outer radius $R_e$ of the sensing element and the inner radius $r_h$ of the housing. With this arrangement, it becomes possible to secure a sufficient clearance necessary for smoothing the insertion of the pushing member which is inserted into the annular end space. Namely, it becomes possible to secure a sufficient clearance between the pushing member and the housing and also secure a sufficient clearance between the pushing member and the sensing element.

Furthermore, the inner radius $r_p$ and the outer radius $R_p$ of the pushing member satisfy the relationship $r_p - R_e \leq 0.375$ mm and $r_h - R_p \leq 0.25$ mm with respect to the outer radius $R_e$ of the sensing element and the inner radius $r_h$ of the housing. With this arrangement, it becomes possible to sufficiently reduce or narrow the clearance between the pushing member and the housing as well as the clearance between the pushing member and the sensing element, when the pushing member is inserted into the annular end space. Accordingly, it becomes possible to uniformly press the hardened powder ring or the inorganic powder in the entire region of the annular end space.

As described above, this invention provides a method for manufacturing a gas sensor capable of uniformly stuffing the inorganic powder into the annular end space defined between the sensing element and the housing without damaging the sensing element and the housing.

According to the above-described first manufacturing method of the present invention, it is preferable that the pushing member has a press portion consisting of a flat surface, an inner curved surface having a curvature radius of 0.3~0.4 mm, and an outer curved surface having a curvature radius of 0.3~0.5 mm. The inner curved surface is formed at a radially inner end of the press portion. The outer curved surface is formed at a radially outer end of the press portion.

When the press portion of the pushing member has inner and outer curved surfaces having the above-described curvature radiuses, the press portion of the pushing member does not hit or collide against the outer surface of the sensing element as well as against the inner surface of the housing. No damage is given to the sensing element and the housing.

As described above, the inner radius $r_p$ and the outer radius $R_p$ of the pushing member satisfy the above-described conditions. The press portion of the pushing member has the inner and outer curved surfaces having the above-described curvature radiuses. Thus, it becomes possible to uniformly stuff the inorganic powder into the annular end space without damaging the sensing element and the housing.

The present invention provides a second method for manufacturing a gas sensor having a tubular housing and a sensing element disposed in the housing, comprising:

a step of inserting the sensing element into the tubular housing from a rear end toward a front end of the housing, the sensing element having a flange portion protruding radially outward from an outer surface thereof, and the housing having an inner cylindrical stepped portion protruding radially inward from an inner cylindrical surface thereof;

a step of placing the flange portion of the sensing element on the inner cylindrical stepped portion of the housing;

a step of inserting a hardened powder ring into an annular end space defined between the inner cylindrical surface of the housing and the outer surface of the sensing element, the hardened powder ring being a hardened block of talc powder configured into a ring shape;

a step of inserting a packing ring in the annular end space to dispose the packing ring on the hardened powder ring, the packing ring being made of an inorganic member different from the hardened powder ring;

a step of inserting a guide into a rear end of the sensing element, the guide being disposed inside an annular pushing member and slidable in an axial direction of the pushing member, a step of sliding the pushing member along the guide toward the front end of the housing, thereby pressing the hardened powder ring via the packing ring by the pushing member and crushing the hardened powder ring into talc powder by the tubular pushing member so that the annular end space is stuffed by the talc powder;

wherein the following relationship is satisfied $$0.275 \text{ mm} \leq r_p - R_e \leq 0.375 \text{ mm},$$

and $$0.15 \text{ mm} \leq r_h - R_p \leq 0.25 \text{ mm},$$

where $r_p$ represents an inner radius of the pushing member, $R_p$ represents an outer radius of the pushing member, $r_h$ represents an inner radius of the housing, and $R_e$ represents an outer radius of the sensing element at a portion substantially defining the annular end space, and the pushing member has a press portion consisting of a flat surface, an inner curved surface having a curvature radius of 0.3~0.4 mm, and an outer curved surface having a curvature radius of 0.3~0.5 mm, the inner curved surface being formed at a radially inner end of the press portion while the outer curved surface being formed at a radially outer end of the press portion.

According to the second manufacturing method of the present invention, it becomes possible to surely manufacture a gas sensor capable of uniformly stuffing the inorganic powder into the annular end space defined between the sensing element and the housing without damaging the sensing element and the housing.

BRIEF DESCRIPTION OF THE DRAWINGS

The above and other objects, features and advantages of the present invention will become more apparent from the following detailed description which is to be read in conjunction with the accompanying drawings, in which:

FIG. 4A is a view explaining an initial condition before a guide is inserted into a sensing element in accordance with the preferred embodiment of the present invention;

FIG. 4B is a view explaining an intermediate condition where the guide is just inserted into the sensing element in accordance with the preferred embodiment of the present invention;

FIG. 4C is a view explaining a last condition where the hardened powder ring and the packing ring are just pressed by the pushing member in accordance with the preferred embodiment of the present invention;

DESCRIPTION OF PREFERRED EMBODIMENT

Figure 1:
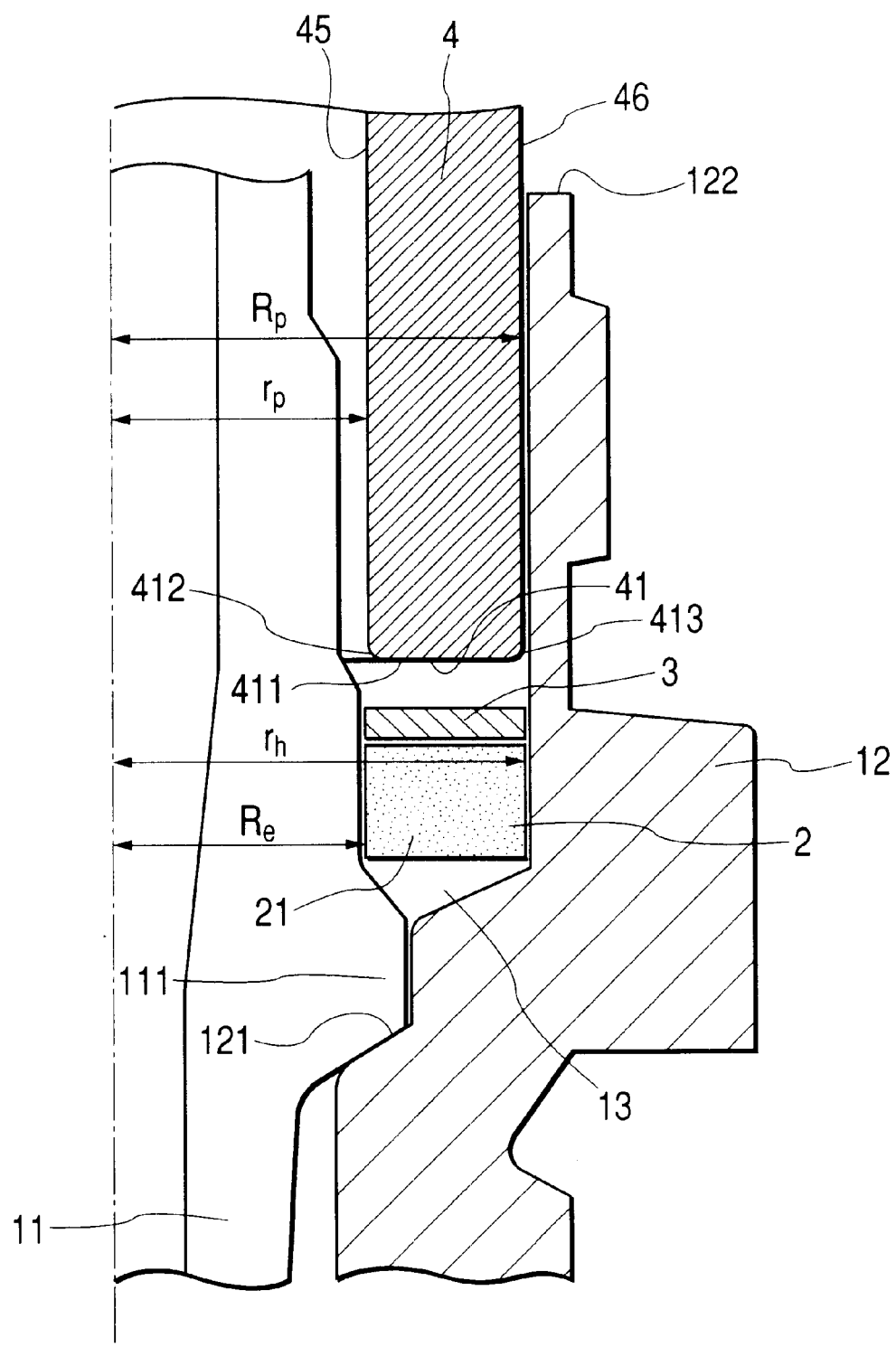
FIG. 1 is a cross-sectional view showing an annular end space into which a hardened powder ring and a packing ring are inserted by a pressing member in accordance with a preferred embodiment of the present invention.

A preferred embodiment of the present invention will be explained hereinafter with reference to attached drawings.

The present invention is applicable, for example, to a gas sensor which measures an oxygen concentration or any other gas concentration to control an air-fuel ratio of an internal combustion engine.

The above-described inner radiuses of the housing and the pushing member represent the distances from their center axes to their inner surfaces. The above-described outer radiuses of the housing and the pushing member represent the distances from their center axes to their outer surfaces. In the following description, the inner and outer radiuses are used in the same manner.

Furthermore, the above-described annular end space is positioned adjacent to a contact portion where the inner cylindrical stepped portion of the housing is brought into contact with the flange portion of the sensing element. The annular end space is an inner dead-end space defined between the inner surface of the housing and the outer surface of the sensing element.

The present invention is characterized in that the inner radius $r_p$ and the outer radius $R_p$ of the pushing member, the outer radius $R_e$ of the sensing element, and the inner radius $r_h$ of the housing satisfy the following relationships:

$$0.275 \text{ mm} \leq r_p - R_e \leq 0.375 \text{ mm},$$

and $$0.15 \text{ mm} \leq r_h - R_p \leq 0.25 \text{ mm}$$

When the inner radius $r_p$ of the pushing member is in a relationship $r_p - R_e < 0.275$ mm with respect to the outer radius $R_e$ of the sensing element constituting a part of the annular end space, it is difficult to secure a sufficient clearance between the pushing member and the sensing element for inserting the pushing member into the annular end space. Accordingly, it will be difficult to smoothly insert the pushing member into the annular end space. On the other hand, in the case of $r_p - R_e > 0.375$ mm, it is difficult to uniformly press the hardened powder ring or the inorganic powder which is placed or stuffed in the annular end space.

When the outer radius $R_p$ of the pushing member is in a relationship $r_h - R_p < 0.15$ mm with respect to the inner radius $r_h$ of the housing constituting a part of the annular end space, it is difficult to secure a sufficient clearance between the pushing member and the housing for inserting the pushing member into the annular end space. Accordingly, it will be difficult to smoothly insert the pushing member into the annular end space. On the other hand, in the case of $r_h - R_p > 0.25$ mm, it is difficult to uniformly press the hardened powder ring or the inorganic powder which is placed or stuffed in the annular end space.

Furthermore, when the inner curved surface formed on the press portion of the pushing member has a curvature radius less than 0.3 mm, the sensing element may be damaged by a sharp edge of the pushing member. On the other hand, when the inner curved surface has a curvature radius larger than 0.4 mm, it will be difficult to apply a sufficient pressing force to the inorganic powder residing in the vicinity of the sensing element. Accordingly, it will be difficult to uniformly press the inorganic powder stuffed into the annular end space.

Furthermore, when the outer curved surface formed on the press portion of the pushing member has a curvature radius less than 0.3 mm, the housing may be damaged by a sharp edge of the pushing member. On the other hand, when the outer curved surface has a curvature radius larger than 0.5 mm, it will be difficult to apply a sufficient pressing force to the inorganic powder residing in the vicinity of the housing. Accordingly, it will be difficult to uniformly press the inorganic powder stuffed into the annular end space.

Furthermore, it is preferable that an inner radius $r_r$ and an outer radius $R_r$ of the hardened powder ring have the following relationship with respect to the outer radius $R_e$ of the sensing element and an inner radius $r_h$ of the housing.

$$0.125 \text{ mm} \leq r_r - R_e \leq 0.225 \text{ mm},$$

and $$0.10 \text{ mm} \leq r_h - R_r \leq 0.20 \text{ mm}.$$

When the inner radius $r_r$ of the hardened powder ring and the outer radius $R_e$ of the sensing element are in the relationship $r_r - R_e < 0.125$ mm, the hardened powder ring may crack when it is inserted into the annular end space. On the other hand, in the case of $r_r - R_e > 0.225$ mm, it will be difficult to sufficiently stuff the inorganic powder in the annular end space.

Furthermore, when the outer radius $R_r$ of the hardened powder ring and the inner radius $r_h$ of the housing are in the relationship $r_h - R_r > 0.2$ mm, the hardened powder ring may crack when it is inserted into the annular end space. On the other hand, in the case of $r_h - R_r > 0.2$ mm, it will be difficult to sufficiently stuff the inorganic powder in the annular end space.

Furthermore, it is preferable that the inorganic powder is talc powder.

Furthermore, it is preferable that the manufacturing method further comprises a step of inserting a packing ring in the annular end space to dispose the packing ring on the hardened powder ring. The packing ring is made of an inorganic member different from the inorganic powder. The pushing member pushes the hardened powder ring via the packing ring.

With this arrangement, it becomes possible to improve the airtightness of the gas sensor.

The above-described packing ring is made of inorganic material such as vermiculite.

Furthermore, it is preferable that an inner radius $r_c$ and an outer radius $R_c$ of the packing ring have the following relationship with respect to the inner radius $r_r$ and the outer radius $R_r$ of the hardened powder ring.

$$r_c \leq r_r \text{ and } R_r \leq R_c$$

With this arrangement, it becomes possible to surely improve the airtightness of the gas sensor.

When the inner radius $r_c$ and the outer radius $R_c$ of the packing ring and the inner radius $r_r$ and the outer radius $R_r$ of the hardened powder ring are in the relationship $r_c > r_r$ or $R_r > R_c$, the airtightness may not be surely improved.

Furthermore, it is preferable that the inner radius $r_c$ and the outer radius $R_c$ of the packing ring have the following relationship with respect to the outer radius $R_e$ of the sensing element and the inner radius $r_h$ of the housing;

$$0.125 \text{ mm} \leq r_c - R_e \leq 0.225 \text{ mm},$$

and $$0.02 \text{ mm} \leq r_h - R_c \leq 0.08 \text{ mm}.$$

When the inner radius $r_c$ of the packing ring and the outer radius $R_e$ of the sensing element are in the relationship $r_c - R_e < 0.125$ mm, the packing ring may crack when it is inserted into the annular end space. On the other hand, in the case of $r_c - R_e > 0.225$ mm, it will be difficult to sufficiently improve the airtightness of the gas sensor.

Furthermore, when the outer radius $R_c$ of the packing ring and the inner radius $r_h$ of the housing are in the relationship $r_h - R_c < 0.02$ mm, the packing ring may crack when it is inserted into the annular end space. On the other hand, in the case of $r_h - R_c > 0.08$ mm, it will be difficult to sufficiently improve the airtightness of the gas sensor.

Furthermore, it is preferable that the pushing member pushes the hardened powder ring under a condition that a center axis of the pushing member agrees with center axes of the housing and the sensing element.

With this arrangement, it becomes possible to surely press the hardened powder ring by the pushing member without damaging the sensing element and the housing.

Furthermore, it is preferable that the pushing member is associated with a guide which is disposed inside the pushing member and is slidable in an axial direction of the pushing member. And, the manufacturing method of this invention further comprises a step of inserting the guide into a rear end (i.e., a rear end opening) of the sensing element, and a step of sliding the pushing member along the guide toward the sensing element, thereby pressing the hardened powder ring by the pushing member.

With this arrangement, it becomes possible to easily press the hardened powder ring under the condition that the center axis of the pushing member agrees with center axes of the housing and the sensing element. Accordingly, the hardened powder ring can be easily pressed by the pushing member without damaging the sensing element and the housing.

A method for manufacturing a gas sensor in accordance with a preferred embodiment of the present invention will be explained with reference to FIGS. 1 to 7.

This embodiment relates to a manufacturing method of a gas sensor 1 having a tubular housing 12 and a sensing element 11 disposed in this housing 12.

The housing 12 has an inner cylindrical stepped portion 121 protruding radially inward from an inner cylindrical surface thereof. The sensing element 11 has a flange portion 111 protruding radially outward from an outer surface thereof.

As shown in FIGS. 3 and 4A–4C, the sensing element 11 is inserted into the housing 12 from its rear end 122 toward its front end 123. The flange portion 111 of the sensing element 11 is placed on the inner cylindrical stepped portion 121 of the housing 12.

Figure 2:
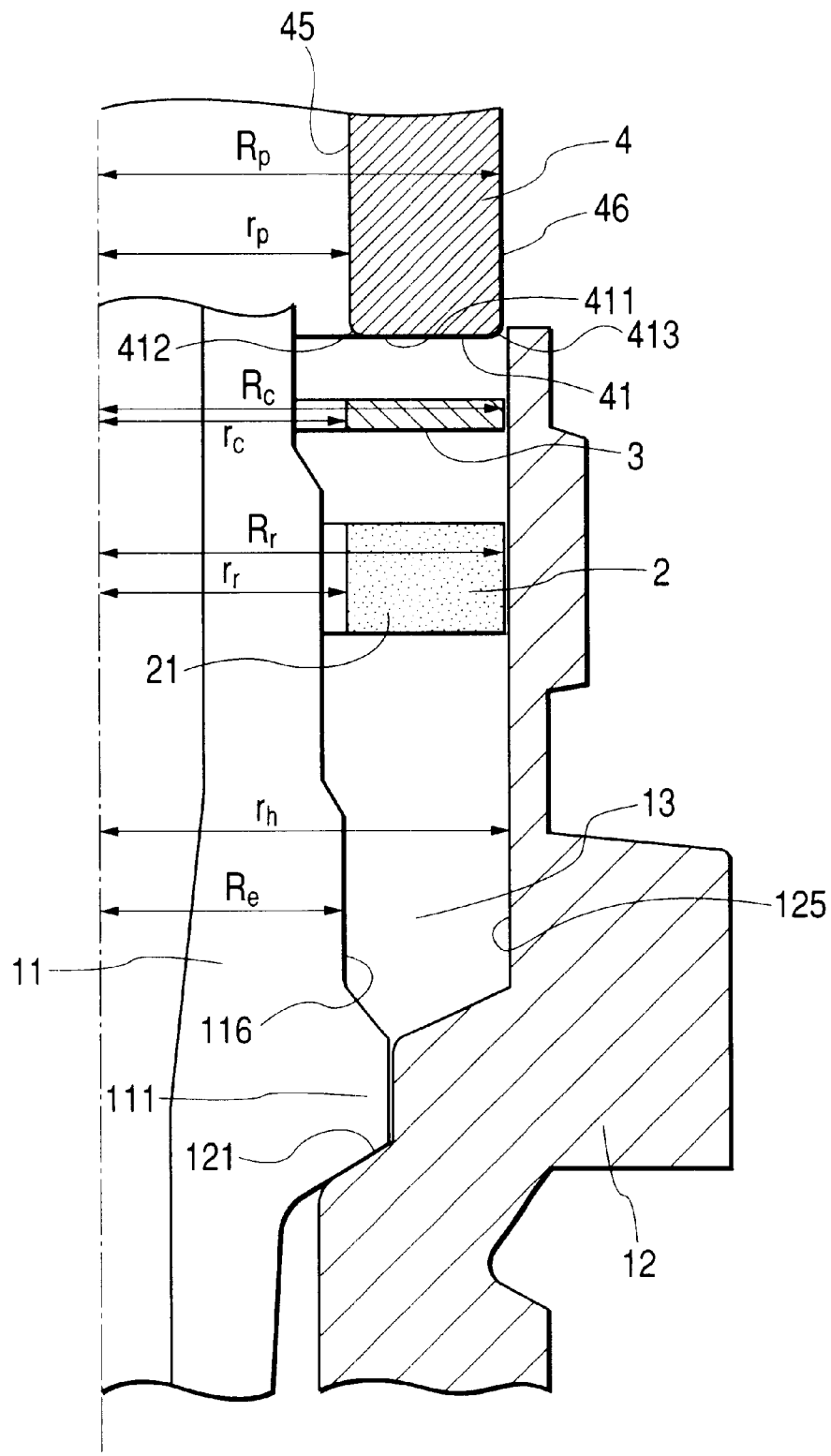
FIG. 2 is a cross-sectional view showing the hardened powder ring and the packing ring before they are inserted into the annular end space by the pressing member in accordance with the preferred embodiment of the present invention.

Next, as shown in FIGS. 1, 2 and 4A, a hardened powder ring 2 is inserted into an annular end space 13 defined between the inner cylindrical surface of housing 12 and the outer surface of sensing element 11. The hardened powder ring 2 is a hardened block of talc powder 21 which is configured into a ring shape (refer to FIGS. 6C and 7B). Then, a packing ring 3 is inserted into the annular end space 13. The packing ring 3 is made of vermiculite and configured into a ring shape (refer to FIGS. 6B and 7A).

Figure 3:
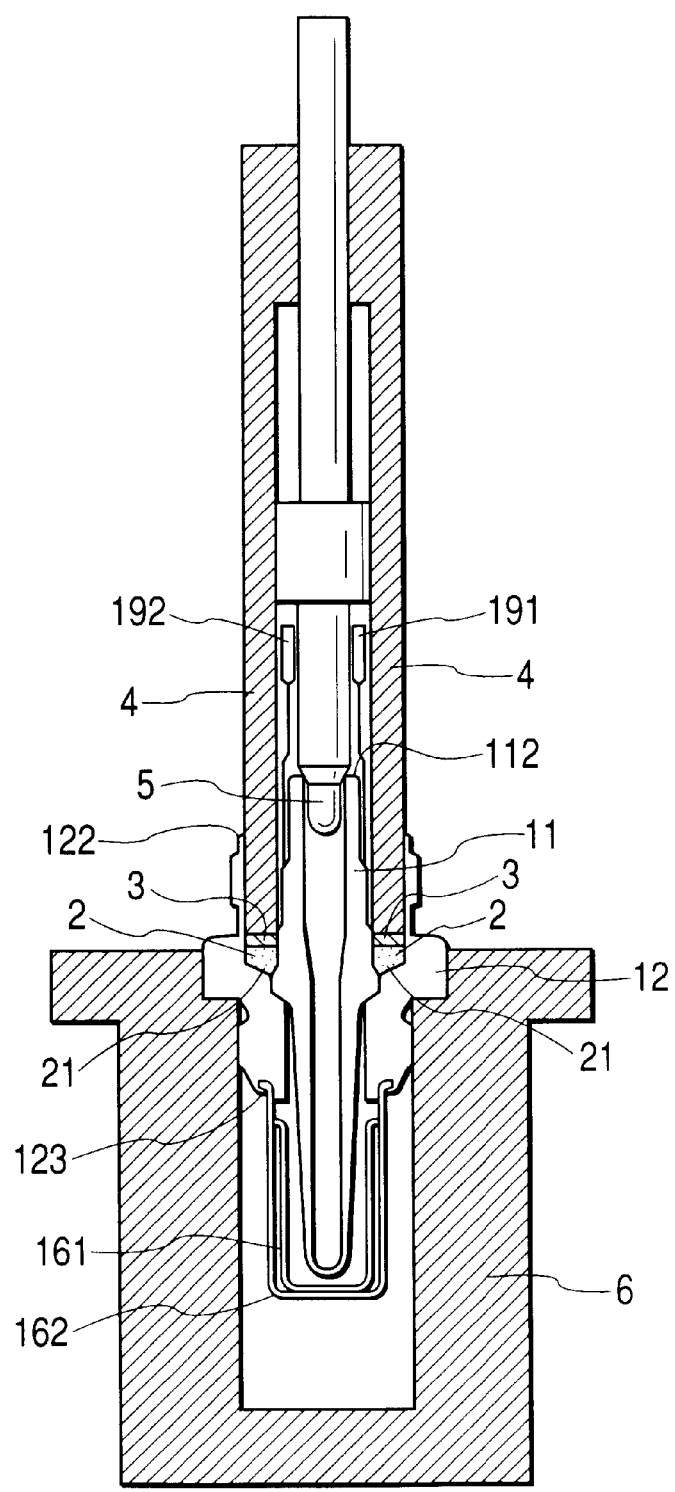
FIG. 3 is a cross-sectional view showing a pushing operation for pressing the hardened powder ring by the pushing member in accordance with the preferred embodiment of the present invention.

Subsequently, as shown in FIGS. 1, 3 and 4C, the hardened powder ring 2 is pressed by the pushing member 4 via the packing ring 3 toward the front end of the housing 12. The pushing member 4 has a tubular shape (refer to FIG. 6A). The hardened powder ring 2 is crashed into talc powder 21.

Figure 5:
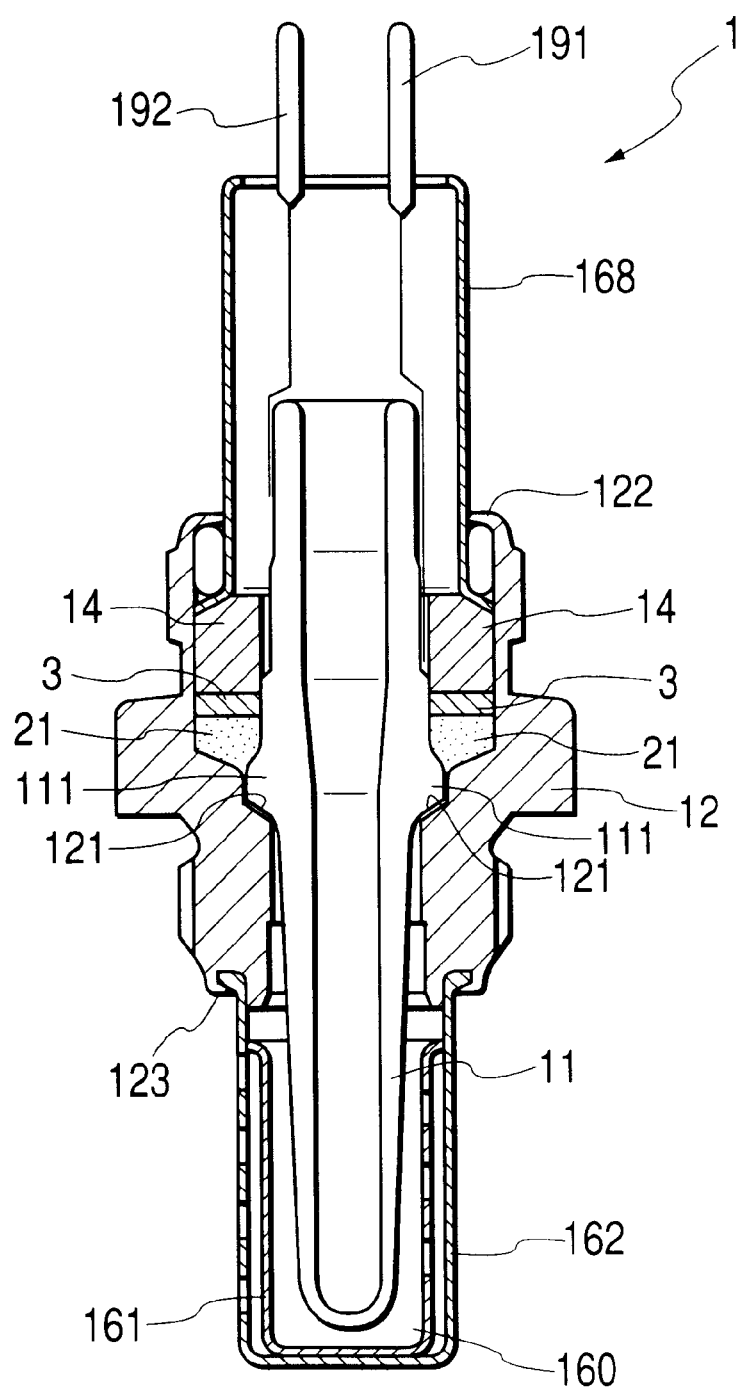
FIG. 5 is a cross-sectional view showing a gas sensor in accordance with the preferred embodiment of the present invention.

Through this pushing operation of the pushing member 4, the talc powder 21 is stuffed into the annular end space 13 as shown in FIG. 5.

As shown in FIGS. 1 and 2, the inner radius $r_p$ and the outer radius $R_p$ of the pushing member 4 have the following relationship with respect to an outer radius $R_e$ of the sensing element 11 and an inner radius $r_h$ of the housing 12;

$$0.275 \text{ mm} \leq r_p - R_e \leq 0.375 \text{ mm},$$

and $$0.15 \text{ mm} \leq r_h - R_p \leq 0.25 \text{ mm}.$$

Furthermore, the pushing member 4 has a press portion 41 consisting of a flat surface 411, an inner curved surface 412 having a curvature radius of 0.3~0.4 mm, and an outer curved surface 413 having a curvature radius of 0.3~0.5 mm. The inner curved surface 412 is formed at a radially inner end of the press portion 41. The outer curved surface 413 is formed at a radially outer end of the press portion 41.

An alternate long and short dash line shown in FIGS. 1 and 2 represents a common center axis of the sensing element 11, the housing 12, the hardened powder ring 2, the packing ring 3, and the pushing member 4.

As shown in FIG. 5, the gas sensor 1 has double-layered exhaust covers 161 and 162 attached to a front end 123 of the housing 12. The double-layered exhaust covers 161 and 162 cooperatively define an exhaust gas chamber 160.

On the other hand, an atmosphere cover 168 is attached to a rear end 122 of the housing 12. Reference numeral 191 represents a minus terminal. Reference numeral 192 represents a plus terminal.

In manufacturing the gas sensor 1, the exhaust covers 161 and 162 are attached to the front end 123 of the housing 12. Then, the exhaust covers 161 and 162 are fastened by caulking. Next, the sensing element 11 is inserted into the housing 12.

Next, as described above, the talc powder 21 and the packing ring 3 are pressed and stuffed into the annular end space 13. Furthermore, a supporter 14 is pressed and stuffed on the packing ring 3. In this case, as shown in FIG. 3, the hardened powder ring 2 is pushed downward under a condition that the housing 12 is held by a holding jig 6.

Thereafter, the atmosphere cover 168 is attached to the rear end 122 of the housing 12 and is fixed by caulking.

Through the above-described manufacturing processes, it becomes possible to obtain the gas sensor 1 shown in FIG. 5.

As shown in FIGS. 3 and 4A to 4C, the pushing operation of hardened powder ring 2 is performed under the condition that a center axis of the pushing member 4 agrees with center axes of the housing 12 and the sensing element 11.

More specifically, as shown in FIGS. 3, 4A to 4C, the pushing member 4 is associated with a guide 5 which is disposed inside the pushing member 4 and is slidable in an axial direction of the pushing member 4. In pushing the hardened powder ring 2, as shown in FIGS. 4A and 4B, the guide 5 is inserted into a rear end 112 of the sensing element 11. Thereafter, as shown in FIG. 4C, the pushing member 4 is slid along the guide 5 toward the sensing element 11, thereby pressing the hardened powder ring 2 via the packing ring 3 by the pushing member 4.

As shown in FIG. 4, the guide 5 has an insertion portion 51, a base portion 52, and a tapered portion 53. The insertion portion 51 has a diameter slightly smaller than an inner diameter of sensing element 11 at its rear end 112. The base portion 52 has a diameter larger than the inner diameter of sensing element 11 at its rear end 112. The tapered portion 53 is formed between the insertion portion 51 and the base portion 52. As shown in FIGS. 4B and 4C, the tapered portion 53 is brought into contact with the rear end 112. In other words, the center axis of pushing member 4 agrees with the center axes of sensing element 11 and the housing 12 by coupling the tapered portion 53 of the guide 5 into the rear end 112 of the sensing element 11. Furthermore, the insertion portion 51 is configured into a semispherical shape so that no damage is given to the rear end 112 of sensing element 11.

Figure 6A:
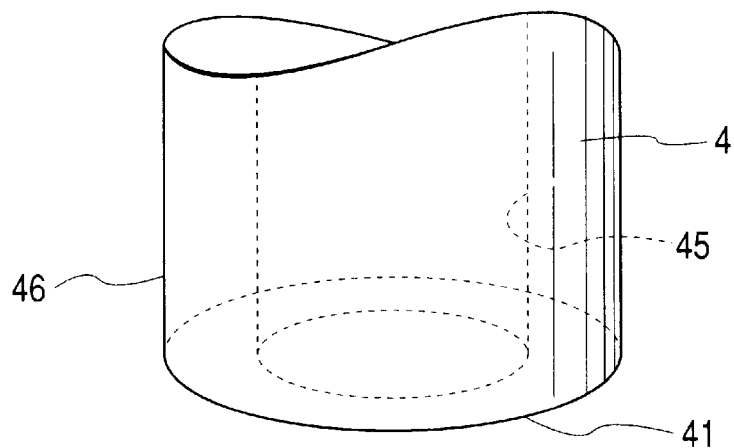
FIG. 6A is a perspective view showing a pushing member in accordance with the preferred embodiment of the present invention.
Figure 6B:
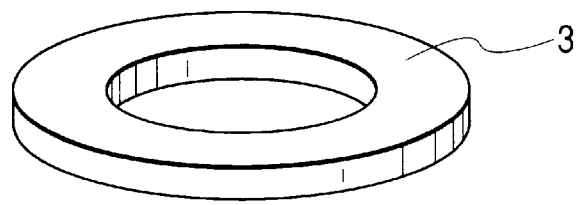
FIG. 6B is a perspective view showing a packing ring in accordance with the preferred embodiment of the present invention.
Figure 6C:
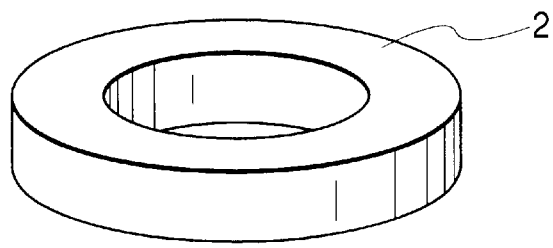
FIG. 6C is a perspective view showing a hardened powder ring in accordance with the preferred embodiment of the present invention.
Figure 7A:
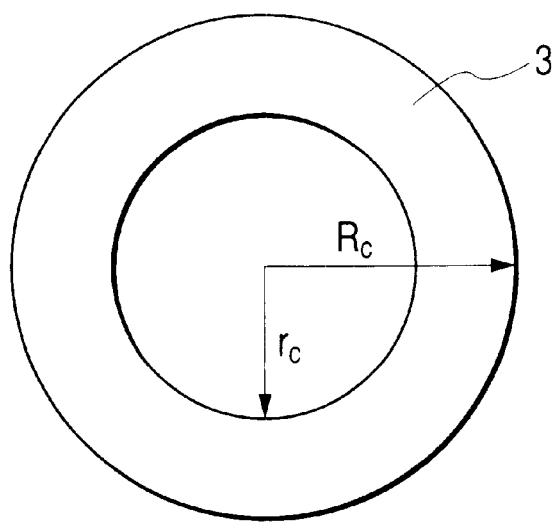
FIG. 7A is a plan view showing the packing ring in accordance with the preferred embodiment of the present invention.
Figure 7B:
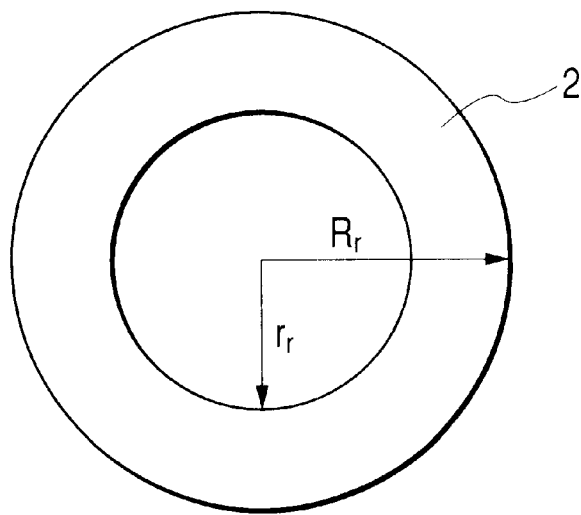
FIG. 7B is a plan view showing the hardened powder ring in accordance with the preferred embodiment of the present invention.

Regarding the size of hardened powder ring 2 shown in FIGS. 6C and 7B, an inner radius $r_r$ and an outer radius $R_r$ of hardened powder ring 2 have the following relationship with respect to the outer radius $R_e$ of sensing element 11 and inner radius $r_h$ of housing 12.

$$0.125 \text{ mm} \leq r_r - R_e \leq 0.225 \text{ mm},$$

and $$0.10 \text{ mm} \leq r_h - R_r \leq 0.20 \text{ mm}.$$

Regarding the size of packing ring 3 shown in FIGS. 6B and 7A, an inner radius $r_c$ and an outer radius $R_c$ of packing ring 3 have the following relationship with respect to the inner radius $r_r$ and the outer radius $R_r$ of hardened powder ring 2.

$$r_c \leq r_r \text{ and } R_r \leq R_c$$

Furthermore, as shown in FIG. 2, the inner radius $r_c$ and the outer radius $R_c$ of packing ring 3 have the following relationship with respect to the outer radius $R_e$ of sensing element 11 and the inner radius $r_h$ of housing 12;

$$0.125 \text{ mm} \leq r_c - R_e \leq 0.225 \text{ mm},$$

and $$0.02 \text{ mm} \leq r_h - R_c \leq 0.08 \text{ mm}.$$

The following is the example of actual size of the pushing member 4, the sensing element 11, the housing 12, the hardened powder ring 2, and the packing ring 3. These size data satisfy all of the above-described relationships.

The inner radius $r_p$ of pushing member 4 is 4.75 mm. The outer radius $R_p$ of punching member 4 is 8.1 mm. The outer radius $R_e$ of sensing element 11 is 4.425 mm. The inner radius $r_h$ of housing 12 is 8.3 mm. The inner radius $r_r$ of hardened powder ring 2 is 4.6 mm. The outer radius $R_r$ of hardened powder ring 2 is 8.15 mm. The inner radius $r_c$ of packing ring 3 is 4.6 mm. The outer radius $R_c$ of packing ring 3 is 8.25 mm.

For example, the curvature radius of inner curved surface 412 is 0.35 mm. The curvature radius of outer curved surface 413 is 0.4 mm.

The above-described embodiment has the following functions and effects.

As described above, the inner radius $r_p$ and the outer radius $R_p$ of pushing member 4 satisfy the relationship $r_p - R_e \geq 0.275$ mm and $r_h - R_p \geq 0.15$ mm with respect to the outer radius $R_e$ of sensing element 11 and the inner radius $r_h$ of housing 12. With this arrangement, it becomes possible to secure a sufficient clearance necessary for smoothing the insertion of the pushing member 4 when the pushing member 4 is inserted into the annular end space 13. Namely, it becomes possible to secure a sufficient clearance between the pushing member 4 and the housing 12 and also secure a sufficient clearance between the pushing member 4 and the sensing element 11.

Furthermore, the inner radius $r_p$ and the outer radius $R_p$ of pushing member 4 satisfy the relationship $r_p - R_e \leq 0.375$ mm and $r_h - R_p \leq 0.25$ mm with respect to the outer radius $R_e$ of sensing element 11 and the inner radius $r_h$ of housing 12. With this arrangement, it becomes possible to sufficiently reduce or narrow the clearance between the pushing member 4 and the housing 12 as well as the clearance between the pushing member 4 and the sensing element 11, when the pushing member 4 is inserted into the annular end space 13. Accordingly, it becomes possible to uniformly press the hardened powder ring 2 or the talc powder 21 in the entire region of the annular end space 13.

Furthermore, as described above, the press portion 41 of pushing member 4 has the inner and outer curved surfaces 412 and 413 having the above-described curvature radiuses. Accordingly, the press portion 41 of pushing member 4 does not hit or collide against the outer surface 116 of sensing element 11 as well as against the inner surface 125 of housing 12. No damage is given to the sensing element 11 and the housing 12.

As described above, the inner radius $r_p$ and the outer radius $R_p$ of pushing member 4 satisfy the above-described conditions. The press portion 41 of pushing member 4 has the inner and outer curved surfaces 412 and 413 having the above-described curvature radiuses. Thus, it becomes possible to uniformly stuff the talc powder 21 into the annular end space 13 without damaging the sensing element 11 and the housing 12.

Furthermore, the packing ring 3 is inserted into the annular end space 13 to dispose the packing ring 3 on the hardened powder ring 2. The pushing member 4 pushes the hardened powder ring 2 via the packing ring 3. With this arrangement, it becomes possible to surely improve the airtightness of gas sensor 1.

Furthermore, the inner radius $r_c$ and the outer radius $R_c$ of packing ring 3 have the relationship $r_c \leq r_r$ and $R_r \leq R_c$ with respect to the inner radius $r_r$ and the outer radius $R_r$ of hardened powder ring 2. With this arrangement, it becomes possible to surely improve the airtightness of gas sensor 1.

Furthermore, the pushing member 4 pushes the hardened powder ring 2 under the condition that the center axis of pushing member 4 agrees with the center axes of housing 12 and sensing element 11. Accordingly, the hardened powder ring 2 can be surely pressed by the pushing member 4 without damaging the sensing element 11 and the housing 12.

Furthermore, the pushing member 4 is associated with the guide 5 which is disposed inside the pushing member 4 and is slidable in the axial direction of the pushing member 4. The guide 5 guides the pushing member 4 when the pushing member 4 presses the hardened powder ring 2. Accordingly, the pushing member 4 can push the hardened powder ring 2 under the condition that the center axis of pushing member 4 agrees with the center axes of housing 12 and sensing element 11. Accordingly, the hardened powder ring 2 can be easily pressed by the pushing member 4 without damaging the sensing element 11 and the housing 12.

As described above, the above-described embodiment of the present invention provides a method for manufacturing a gas sensor capable of uniformly stuffing the inorganic powder into the annular end space defined between the sensing element and the housing without damaging the sensing element and the housing.

This invention may be embodied in several forms without departing from the spirit of essential characteristics thereof. The present embodiment described is therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A method for manufacturing a gas sensor having a tubular housing and a sensing element disposed in said housing, comprising:

a step of inserting said sensing element into said tubular housing from a rear end toward a front end of said housing, said sensing element having a flange portion protruding radially outward from an outer surface thereof, and said housing having an inner cylindrical stepped portion protruding radially inward from an inner cylindrical surface thereof;

a step of placing said flange portion of said sensing element on said inner cylindrical stepped portion of said housing;

a step of inserting a hardened powder ring into an annular end space defined between the inner cylindrical surface of said housing and the outer surface of said sensing element, said hardened powder ring being a hardened block of inorganic powder configured into a ring shape;

a step of pressing said hardened powder ring toward the front end of said housing by a tubular pushing member and crushing said hardened powder ring into inorganic powder by said tubular pushing member so that said annular end space is stuffed by the inorganic powder;

wherein the following relationship is satisfied $$0.275 \text{ mm} \leq r_p - R_e \leq 0.375 \text{ mm},$$

and $$0.15 \text{ mm} \leq r_h - R_p \leq 0.25 \text{ mm},$$

where $r_p$ represents an inner radius of said pushing member, $R_p$ represents an outer radius of said pushing member, $r_h$ represents an inner radius of said housing, and $R_\theta$ represents an outer radius of said sensing element at a portion substantially defining said annular end space.

2. The method for manufacturing a gas sensor in accordance with claim 1, wherein said pushing member has a press portion consisting of a flat surface, an inner curved surface having a curvature radius of 0.3~0.4 mm, and an outer curved surface having a curvature radius of 0.3~0.5 mm, said inner curved surface being formed at a radially inner end of said press portion while said outer curved surface being formed at a radially outer end of said press portion.

3. The method for manufacturing a gas sensor in accordance with claim 1, wherein an inner radius $r_r$ and an outer radius $R_r$ of said hardened powder ring have the following relationship with respect to the outer radius $R_e$ of said sensing element and an inner radius $r_h$ of said housing;

$$0.125 \text{ mm} \leq r_r - R_e \leq 0.225 \text{ mm},$$

and $$0.10 \text{ mm} \leq r_h - R_r \leq 0.20 \text{ mm}.$$

4. The method for manufacturing a gas sensor in accordance with claim 1, wherein said inorganic powder is talc powder.

5. The method for manufacturing a gas sensor in accordance with claim 1, further comprising
a step of inserting a packing ring in said annular end space to dispose said packing ring on said hardened powder ring, said packing ring being made of an inorganic member different from said inorganic powder,
wherein said pushing member pushes said hardened powder ring via said packing ring.

6. The method for manufacturing a gas sensor in accordance with claim 5, wherein an inner radius $r_c$ and an outer radius $R_c$ of said packing ring have the following relationship with respect to the inner radius $r_r$ and the outer radius $R_r$ of said hardened powder ring, $$r_c \leq r_r \text{ and } R_r \leq R_c.$$

7. The method for manufacturing a gas sensor in accordance with claim 5, wherein an inner radius $r_c$ and an outer radius $R_c$ of said packing ring have the following relationship with respect to the outer radius $R_e$ of said sensing element and the inner radius $r_h$ of said housing;

$$0.125 \text{ mm} \leq r_c - R_e \leq 0.225 \text{ mm},$$

and $$0.02 \text{ mm} \leq r_h - R_c \leq 0.08 \text{ mm}.$$

8. The method for manufacturing a gas sensor in accordance with claim 1, wherein said pushing member pushes said hardened powder ring under a condition that a center axis of said pushing member agrees with center axes of said housing and said sensing element.

9. The method for manufacturing a gas sensor in accordance with claim 8, wherein said pushing member is associated with a guide which is disposed inside said pushing member and is slidable in an axial direction of said pushing member, and said manufacturing method further comprises:
a step of inserting said guide into a rear end of said sensing element, and
a step of sliding said pushing member along said guide toward said sensing element, thereby pressing said hardened powder ring by said pushing member.

10. A method for manufacturing a gas sensor having a tubular housing and a sensing element disposed in said housing, comprising:

a step of inserting said sensing element into said tubular housing from a rear end toward a front end of said housing, said sensing element having a flange portion protruding radially outward from an outer surface thereof, and said housing having an inner cylindrical stepped portion protruding radially inward from an inner cylindrical surface thereof;

a step of placing said flange portion of said sensing element on said inner cylindrical stepped portion of said housing;

a step of inserting a hardened powder ring into an annular end space defined between the inner cylindrical surface of said housing and the outer surface of said sensing element, said hardened powder ring being a hardened block of talc powder configured into a ring shape;

a step of inserting a packing ring in said annular end space to dispose said packing ring on said hardened powder ring, said packing ring being made of an inorganic member different from said hardened powder ring, a step of inserting a guide into a rear end of said sensing element, said guide being disposed inside an annular pushing member and slidable in an axial direction of said pushing member, a step of sliding said pushing member along said guide toward the front end of said housing, thereby pressing said hardened powder ring via said packing ring by said pushing member and crushing said hardened powder ring into talc powder by said tubular pushing member so that said annular end space is stuffed by the talc powder;

wherein the following relationship is satisfied $$0.275 \text{ mm} \leq r_p - R_e 0.375 \text{ mm},$$

and $$0.15 \text{ mm} \leq r_h - R_p \leq 0.25 \text{ mm},$$

where $r_p$ represents an inner radius of said pushing member, $R_p$ represents an outer radius of said pushing member, $r_h$ represents an inner radius of said housing, and $R_e$ represents an outer radius of said sensing element at a portion substantially defining said annular end space, and said pushing member has a press portion consisting of a flat surface, an inner curved surface having a curvature radius of 0.3~0.4 mm, and an outer curved surface having a curvature radius of 0.3~0.5 mm, said inner curved surface being formed at a radially inner end of said press portion while said outer curved surface being formed at a radially outer end of said press portion.

* * * * *